United States Patent
Dorey et al.

(10) Patent No.: US 12,383,638 B2
(45) Date of Patent: Aug. 12, 2025

(54) METHOD FOR STERILIZING AN ASSEMBLY COMPRISING AT LEAST ONE SINGLE-USE DEVICE FOR BIOPHARMACEUTICAL FLUID

(71) Applicant: SARTORIUS STEDIM FMT SAS, Aubagne (FR)

(72) Inventors: Samuel Dorey, Le Beausset (FR); Marie-Christine Menier, La Ciotat (FR); Lara Nascimento-Brooks, Hitchin (GB)

(73) Assignee: SARTORIUS STEDIM FMT SAS, Aubagne (FR)

( * ) Notice: Subject to any disclaimer, the term of this patent is extended or adjusted under 35 U.S.C. 154(b) by 0 days.

(21) Appl. No.: 18/556,238

(22) PCT Filed: Apr. 21, 2022

(86) PCT No.: PCT/FR2022/000036
§ 371 (c)(1),
(2) Date: Oct. 19, 2023

(87) PCT Pub. No.: WO2022/223885
PCT Pub. Date: Oct. 27, 2022

(65) Prior Publication Data
US 2024/0082439 A1    Mar. 14, 2024

(30) Foreign Application Priority Data
Apr. 23, 2021 (FR) .................. FR2104255

(51) Int. Cl.
*A61L 2/08* (2006.01)
*A61L 2/28* (2006.01)
(Continued)

(52) U.S. Cl.
CPC .................. *A61L 2/082* (2013.01); *A61L 2/28* (2013.01); *B01F 23/23313* (2022.01);
(Continued)

(58) Field of Classification Search
CPC ........ A61L 2/082; A61L 2/28; A61L 2202/14; A61L 2202/181; A61L 2202/25;
(Continued)

(56) References Cited

U.S. PATENT DOCUMENTS 3,209,905 A * 10/1965 Kean, Sr. ............. B65D 88/528
                                                        206/451
3,621,638 A * 11/1971 Grocke .................. B65B 9/135
                                                        53/567
(Continued)

FOREIGN PATENT DOCUMENTS

DE   102019109210 A1   10/2020
WO      2017021653 A1    2/2017

OTHER PUBLICATIONS

International Search Report for International Application No. PCT/FR2022/000036 mailed on Jul. 21, 2022.
(Continued)

*Primary Examiner* — Regina M Yoo
(74) *Attorney, Agent, or Firm* — Heslin Rothenberg Farley & Mesiti P.C.

(57) ABSTRACT

A method for sterilizing by X-rays an assembly containing a single-use device intended to receive a biopharmaceutical fluid, comprising: placing a plurality of dosimeters, repeatedly passing the assembly in front of the X-ray radiation window, according to a first face then according to a second face of the assembly, at several irradiation power-time pairs (PTi), followed by mapping the radiation dose; and —determining an optimum power-time pair (PTopt) for which the mapping reveals that all dosimeters have recorded a
(Continued)

radiation dose above a minimum sterility dose (Dmin), and for which the dosimeter associated with a fragile element of the single-use device records a radiation dose below a maximum dose (Dmax) defined as being the dose from which the X-ray irradiation deteriorates the fragile element.

19 Claims, 3 Drawing Sheets

(51) Int. Cl.
    *B01F 23/233*     (2022.01)
    *B01F 23/237*     (2022.01)
    *B01F 27/113*     (2022.01)
    *B01F 27/191*     (2022.01)
    *B01F 27/906*     (2022.01)
    *B01F 35/513*     (2022.01)
    *C12M 1/00*     (2006.01)
    *C12M 1/06*     (2006.01)
    *C12M 1/12*     (2006.01)
    *B01F 101/22*     (2022.01)

(52) U.S. Cl.
    CPC .. *B01F 23/23362* (2022.01); *B01F 23/23761* (2022.01); *B01F 27/113* (2022.01); *B01F 27/191* (2022.01); *B01F 27/906* (2022.01); *B01F 35/513* (2022.01); *C12M 23/14* (2013.01); *C12M 23/28* (2013.01); *C12M 27/02* (2013.01); *C12M 37/00* (2013.01); *A61L 2202/14* (2013.01); *A61L 2202/181* (2013.01); *A61L 2202/25* (2013.01); *B01F 2101/22* (2022.01)

(58) Field of Classification Search
    CPC .............. A61L 2/0041; A61L 2202/21; A61L 2202/22; A61L 2202/23; B01F 23/23313; B01F 23/23362; B01F 23/23761; B01F 27/113; B01F 27/191; B01F 27/906; B01F 35/513; B01F 2101/22; C12M 23/14; C12M 23/28; C12M 27/02; C12M 37/00; C12M 37/06

See application file for complete search history.

(56) References Cited

U.S. PATENT DOCUMENTS

| | | | | |
|---|---|---|---|---|
| RE32,344 E | * | 2/1987 | Wind | B65D 19/06 217/43 A |
| 5,370,233 A | * | 12/1994 | Schutz | B65D 5/322 206/386 |
| 5,413,224 A | * | 5/1995 | Marron | B65D 19/18 206/335 |
| 6,427,842 B1 | * | 8/2002 | Green | B65D 75/32 53/442 |
| 7,823,725 B1 | * | 11/2010 | Shupe | B65D 71/0096 206/509 |
| 2004/0020820 A1 | * | 2/2004 | Stephens | B65D 5/503 206/592 |
| 2004/0033160 A1 | | 2/2004 | MacPhee et al. | |
| 2004/0040263 A1 | * | 3/2004 | Lauder | B29C 70/66 53/471 |
| 2005/0053194 A1 | | 3/2005 | Stichelbaut | |
| 2008/0135698 A1 | * | 6/2008 | Gordon | A47F 1/12 211/126.15 |
| 2012/0075071 A1 | * | 3/2012 | Liu | B65D 19/001 235/492 |
| 2013/0139618 A1 | | 6/2013 | Chaussin et al. | |
| 2014/0154808 A1 | * | 6/2014 | Patel | A61L 2/28 436/1 |
| 2015/0344161 A1 | * | 12/2015 | Selker | B65B 55/02 422/534 |
| 2019/0329197 A1 | | 10/2019 | Chaussin et al. | |
| 2021/0139215 A1 | * | 5/2021 | Gilligan | B65D 1/36 |

OTHER PUBLICATIONS

Written Opinion for International Application No. PCT/FR2022/000036 mailed on Jul. 21, 2022.

French Search Report issued in FR2104255 and mailed Dec. 10, 2021.

\* cited by examiner

METHOD FOR STERILIZING AN ASSEMBLY COMPRISING AT LEAST ONE SINGLE-USE DEVICE FOR BIOPHARMACEUTICAL FLUID

CROSS REFERENCE TO RELATED APPLICATIONS

This application is a national stage filing under section 371 of International Application No. PCT/FR2022/000036, filed on Apr. 21, 2022, published on Oct. 27, 2022 as WO 2022/223885 A1 which claims priority to French Patent Application No. FR2104255, filed on Apr. 23, 2021. The entire disclosures of each application are hereby incorporated herein by reference.

TECHNICAL FIELD

The present disclosure relates to the field of sterilization of single-use devices intended to receive biopharmaceutical fluid, and more particularly, sterilization by X-rays of pallets or nacelles containing one or more single-use container(s) intended to receive a biopharmaceutical fluid, i.e. a product derived from biotechnology (culture media, cell cultures, buffer solutions, artificial nutrition liquids, blood products and blood product derivatives) or a pharmaceutical product or more generally a product intended for use in the medical field.

PRIOR ART

A biopharmaceutical bioreactor type pouch (or container) is a device that supports a biologically active environment. It may be composed of a film, polycarbonate, polyethylene or polypropylene envelope and comprises a tank intended to receive biopharmaceutical or biological products.

The bioreactor may contain different sensors, like temperature or pressure sensors, to monitor the evolution of the biologically active environment. The size of the bioreactor is variable and may commonly range from 50 to 2,000 L.

Before commercialization, the bioreactor is conventionally irradiated by means of gamma rays in order to destroy micro-organisms that might be present and which could distort the functioning of the bioreactor afterwards. Gamma radiation is electromagnetic radiation emitted during the decay of a radioactive source, cobalt 60. The energy of the emitted radiation allows destroying the micro-organisms and, at some doses, could allow sterilizing a product. To sterilize the products, they are automatically conveyed through an irradiation cell. The products are often already packed, and superimposed on a tray of a pallet or a nacelle to form a set of products that enables them to be transported in batches. The assembly then receives a controlled dose of gamma rays, before being transported out of the irradiation cell. The assembly may undergo several irradiations, for example, according to several faces, by rotating the assembly on itself, to ensure that all portions of the assembly have received the irradiation. The energy absorbed during radiation is measured in kilogray (kGy). This absorbed energy, measured using a dosimeter, depends on several factors, including the exposure duration, the radiation intensity, the material density and the size of the package.

In the case where the gamma radiation is at too high a dose, it might damage and even destroy some components of the bioreactor, such as the sensors, for example. Therefore, at present, treatment with gamma rays does not, strictly speaking, enable sterilization of bioreactors. Indeed, the relative fragility of the sensors in these containers does not enable irradiating it at a dose that would enable sterilization, but is confined to a dose below it. We then simply talk about "irradiated container". This irradiation certainly allows for a relative sterility (i.e. about 1 organism out of 100,000 survives), but it does not allow complying with the standard ISO11137 of sterility in the health environment (i.e. about 1 organism out of 1 million survives).

SUMMARY

The present disclosure improves the situation.

A method is provided for the sterilization by X-rays of an assembly comprising a support and a single-use device intended to receive a biopharmaceutical fluid, the density of the assembly being heterogeneous, the assembly having a height of 65% or more of a size of an X-ray radiation window, the height being considered according to a direction normal to the support, the single-use device comprising a sensor and a mixing device, the method comprising: —placing a plurality of dosimeters distributed on and/or in the single-use device according to a predefined arrangement, a dosimeter being arranged on the sensor and/or on a port of the sensor, and another dosimeter being arranged on the mixing system, —forming the assembly according to a predefined configuration by arrangement of the single-use device equipped with the plurality of dosimeters in a package on the support, —repeating a passage of the assembly in front of the X-ray radiation window, according to a first face then according to a second face of the assembly, with several irradiation power-time pairs, while incrementing the power-time pair between a minimum power-time pair and a maximum power-time pair, followed by a mapping of the irradiation dose received by each of the plurality of dosimeters for each of the incremented power-time pairs, the first face and the second face containing the height of the assembly, its second face being opposite to the first face; and— determining an optimum X-ray radiation power-time pair for which the mapping reveals that after passage according to the first face and according to the second face, all dosimeters record an irradiation dose above a minimum dose and the dosimeter associated with the sensor records an irradiation dose below a maximum dose, the minimum irradiation dose being defined as the dose from which sterility is effective, and the maximum irradiation dose being defined as being the dose from which X-ray irradiation deteriorates the sensor.

In the case of a container for example, because of the presence of elements with different materials (for example a shaft of the mixing device is made of polyethylene terephthalate while a wall of the container is made of polypropylene, or ball bearings which may contain ceramic and/or metal elements), the density of the container, and consequently of the assembly, is heterogeneous. Thus, for a given radiation, the received radiation dose may vary from one point of the container to another. A denser material will receive a lower irradiation dose than a less dense material. Consequently, sterility may not be assured everywhere if an insufficient dose is received in high-density areas of the assembly. A material is said to have a high density when its density is higher than 0.6 g/cm$^3$. On the other hand, the container includes fragile elements, such as the sensor, which may be damaged if an excessively high irradiation dose is applied. Hence, the method takes these parameters into account to enable an assembly comprising one (or several packages) each comprising one (or more) container(s) to be sterilized in a minimum of passages. This is all the more relevant when the assembly has a height 65% or more as large as a size of an X-ray radiation window. According to one embodiment, the assembly has a height 65% or more as large as a size of an X-ray radiation window. According to one embodiment, the assembly has a height 70% or more as large as a size of an X-ray radiation window. According to one embodiment, the assembly has a height 75% or more as large as a size of an X-ray radiation window. In one embodiment, the assembly has a height 80% or more as large as a size of an X-ray radiation window. In one embodiment, the assembly has a height 85% or more as large as a size of an X-ray radiation window. In one embodiment, the assembly has a height 90% or more as large as a size of an X-ray radiation window. In this case, the radiation window may create edge effects, i.e. areas around the periphery of the radiation window that do not receive the prescribed irradiation. The method disclosed herein also allows overcoming, at least partially, these edge effects.

The features disclosed in the next paragraphs may, optionally, be implemented. They may be implemented independently of each other or in combination with each other:

the method further comprises a prior step of determining the maximum dose and/or determining the minimum dose.

the single-use device contains a plurality of sensitive elements, the sensitive elements being defined as elements that deteriorate beyond a predetermined irradiation dose, the sensor forming part of the plurality of sensitive elements, and wherein the step of placing the dosimeters comprises placing a dosimeter on each of the plurality of sensitive elements, and in the step of determining the optimum X-ray radiation power-time pair, the optimum power-time pair is the pair for which the mapping reveals that all dosimeters record an irradiation dose above the minimum dose and that the dosimeters associated with the sensitive elements record an irradiation dose below the maximum dose, and the maximum dose being defined as being the lowest dose from which the X-ray irradiation destroys the functionality of one of the sensitive elements.

before each passage of the assembly in front of the radiation window at a given irradiation power-time pair, a new plurality of dosimeters that have not yet been irradiated is placed on a new single-use device which has not yet been irradiated in the predetermined arrangement to form a new assembly which has not yet been irradiated.

before each passage of the assembly according to the second face in front of the radiation window at a given irradiation power-time pair, a new plurality of dosimeters that have not yet been irradiated are placed on a new single-use device which has not yet been irradiated at the predetermined arrangement to form a new assembly which has not yet been irradiated the minimum irradiation dose is defined by the standard ISO11137.

the minimum irradiation dose is at least 25 kGy, preferably at least 27.5 kGy and still more preferably at least 30 kGy.

the maximum irradiation dose is comprised between 45 and 50 kGy, preferably 47 kGy.

the power-time pairs are pairs taken from among combinations of irradiation power and irradiation time between a minimum power of 75 kW and a maximum power of 1,100 kW, and a minimum irradiation time of 0.1 h and a maximum irradiation time of 20 h.

the time increment of the irradiation is done in increments comprised between 0.1 h and 2 h.

the power increment of the irradiation is done in increments comprised between 50 and 200 kW.

this method further comprises the repetition of a passage of the assembly in front of the radiation window according to two other opposite faces of the assembly.

the package comprises several single-use devices and/or the assembly comprises several packages arranged on the support.

the method further comprises the irradiation at the optimum power-time pair of a new assembly comprising a new package and a new single-use device with shapes and sizes identical to those of the previous steps, the single-use device and the package being arranged in the predetermined configuration, the irradiation taking place according to its first face then the second face of the assembly.

According to another aspect, an assembly is provided comprising: —a support on which rests a package containing a single-use device intended to receive a biopharmaceutical fluid, the density of the assembly being heterogeneous, the assembly having a height of 65% or more of an X-ray radiation window size, the single-use device comprising a sensor and a mixing device, the assembly being sterilized according to the method hereinabove.

BRIEF DESCRIPTION OF THE DRAWINGS

Other features, details and advantages will appear upon reading the detailed description hereinafter, and upon analyzing the appended drawings, wherein.

DESCRIPTION OF THE EMBODIMENTS

Figure 1:
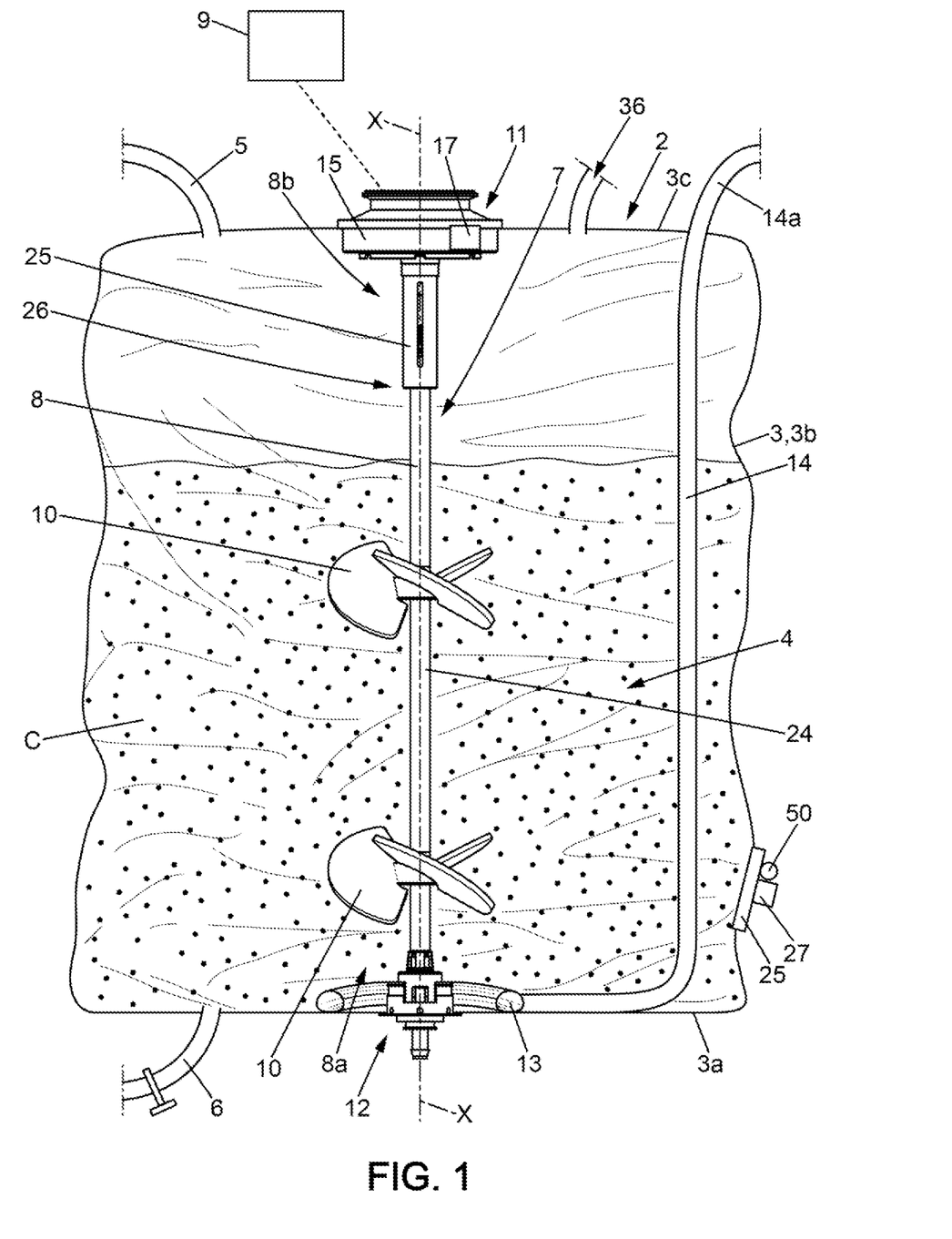
FIG. 1 is a schematic view of a single-use device intended to receive a biopharmaceutical fluid, according to one embodiment.

Reference is now made to FIG. 1, which shows a schematic view of an example of a single-use device 2 receiving a biopharmaceutical fluid C. The single-use device may be a pouch or a container, or a filter. When the pouch or container 2 is intended for a chemical reaction, the container 2 may then be called a "bioreactor".

The single-use device 2 may be intended to receive the biopharmaceutical fluid C for transport operations, cell culture, mixing and/or chemical reactions, and/or filtration. The biopharmaceutical fluid may be a product resulting from biotechnology—culture media, cell cultures, buffer solutions, artificial nutrition liquids, blood products and derivatives of blood products—or a pharmaceutical product or more generally a product intended for use in the medical field.

According to one embodiment, the single-use device 2 is a container 2 formed by a wall 3, preferably made of a plastic material, for example polycarbonate, polyethylene, or polypropylene. The wall 3 is flexible and impermeable to the biopharmaceutical fluid C. The wall 3 of the container 2 may comprise a lower portion 3a, a lateral portion 3b and an upper portion 3c, for example formed by one or more section(s) secured, welded, together. Thus, the container 2 delimits an internal space 4, able to receive a given amount of the biopharmaceutical fluid C. The wall 3 may be completely or partially transparent or translucent in order to be able to observe from the outside the biopharmaceutical fluid C in the internal space 4.

The container 2 is intended for one single use, and may have a capacity comprised between 10 and 5,000 liters, depending on needs and applications. According to another embodiment, the capacity of the container 2 is 10, 50, 100, 200, 1,000, 2,000 or 5,000 liters.

The container 2 has a main axis XX according to which it extends. The container 2 may be made so that the internal space 4 has a more or less cylindrical, rectangular and even somehow flat shape, in particular for the pouches with small volumes.

Depending on its size, the container 2 may be more or less complex and contain more or fewer components. At least the container 2 comprises a sensor 27 and a device 7 for mixing the biopharmaceutical fluid C. The container 2 may comprise several sensors 27 (for example contact sensors, optical sensors, temperature sensors, pressure sensors) and/or several mixing devices 7. The sensor 27 and the mixing device 7 will be described in more detail hereinbelow.

The container 2 may comprise one or more through port(s) 5 for introducing the biopharmaceutical fluid C or components of the biopharmaceutical fluid C, cooperating with one or more inlet orifice(s) formed in the container 2. The container 2 may also comprise at least one through port 6 for emptying the fluid biopharmaceutical C, cooperating with at least one drain orifice formed in the container 2. The drain port 6 could be closed whenever necessary and, on the contrary, opened for draining. By "port", it should be understood a physical connection or link means. Such a port is through when it comes to ensuring a communication function between the internal space 4 and the outside of the container 2, for example for the introduction or emptying of what should be placed or is placed in the container 2. Such a port may also be non-through when it comes to ensuring a function of maintaining a member of the mixing vessel. Ducts, pouches, reservoirs, flexible where appropriate, may be associated with the inlet port, in fluid communication and with a sealed and, where appropriate, removable connection. Similarly, ducts, pouches, reservoirs, flexible where appropriate, may be associated with the drain port 6, in fluid communication and with a sealed and, where appropriate removable, connection. In the embodiment shown in FIG. 1, the lowest of the container 2. However, this embodiment is not restrictive and one or more inlet port(s) may be located in the lower portion 3a or in the lateral portion 3b of the container 2. The container 2 may also include an aeration device 13 able to deliver a given amount of aeration gas to the biopharmaceutical fluid C. Thus, this device 13 enables aeration 10 of what is in the internal space 4 of the container 2, whether it is the biopharmaceutical fluid C, or part of its components. The aeration device 13 may comprise an aeration gas supply device 14 having at least one tubular element 14a extending in fluid communication from the outside of the container 2. The aeration device 13 may be functionally associated with at least one aeration gas discharge port 36 formed in the upper portion 3c of the wall 3 of the container 2. Such a ventilation gas discharge port 36 allows evacuating from the container 2, to the outside, the gas that has not been mixed with the biopharmaceutical fluid C of the container 2. In some embodiments, the container 2 may also include other ports known per se, for example for mounting a functional means, capable of ensuring the maintenance of a member such as typically collecting or measuring data, or drawing samples for analysis.

The mixing device 7 enables mixing of what is in the internal space 4 of the container 2, whether it is the biopharmaceutical fluid C, or part of its components. The mixing device 7 comprises at least one shaft 8, able to be driven, in particular magnetically, in rotation by a motor 9 and to drive in rotation at least one mixing member 10 mounted on the shaft 8. The mixing member(s) 10 are substantially spaced apart from the lower portion 3a and from the lateral portion 3b of the wall 3 of the container 2. The mixing member 10 may be in the form of a propeller having a hub supporting several blades. The shaft 8 may have a fixed length or have an adjustable length. The shaft 8 may be rotated by the motor 9 (partially shown in FIG. 2), outside the container 2.

The container 2 also comprises at least one first bearing 11, adjacent to the upper portion 3c of the wall 3, with which the upper portion 8b of the shaft 8 cooperates. The first bearing 11 comprises a rigid collar. By "collar", it should be herein understood a rigid portion in the general shape of a solid wall, at least substantially planar, laid flat, and intended for maintenance. This collar is rigidly and tightly fastened to the upper portion 3c of the wall 3 of the container 2. More specifically, the collar is made of a substantially rigid material, preferably a rigid plastic material, in the form of a wall or plate connected to the container 2, at the center of the upper portion 3c. This collar may be connected to the wall 3 of the container 2 in any suitable way so as to form a rigid and hermetic joint between the respective rigid and flexible materials of the collar and of the wall 3.

According to one embodiment, the shaft 8 of the mixing device 7 is located entirely in the internal space 4. Thus, the shaft 8 extends straight between a lower end 8a and an upper end 8b. When the container 2 is in a position suitable for operation thereof, the shaft 8 extends vertically according to the main axis XX, the lower end 8a being located towards the lower portion 3a of the container 2 whereas the upper end 8b is located towards the upper portion 3c of the container 2.

According to one embodiment, the drive motor 9 allows magnetically driving the shaft 8 in rotation. To this end, the engine 9 comprises a driving rotary disc located outside the container 2. The shaft 8 then comprises a driven rotary disc 15 intended to cooperate functionally, in particular magnetically, with the driving rotary disc 30 of the motor 9. More particularly, the driven rotary disc 15 comprises a plurality of magnets 17, which are integrated by any fastening or construction means, in order to enable the rotation of the shaft 8 during the rotation of the driving rotary disc of the motor 9. The driven rotary disc 15 is secured, in particular in rotation, to the shaft 8.

According to one embodiment, the container 2 comprises an attachment, or port 25 for fastening the sensor 27 to the wall 3. According to one embodiment, the sensor 27 is a probe by contact with the biopharmaceutical fluid C, and the attachment 25 is an annular part which surrounds a measurement port, and protects the sensor 27. This measurement port may be separate from the port 5 and the drain port 6. The sensor 27 may be a contact probe which allows measuring parameters relating to the biopharmaceutical fluid C which will be found without the internal space 4 of the container 2, such as pressure, pH, temperature, colorimetry, biomass or conductimetry. Other types of sensors may be considered for the container 2, such as, for example, optical sensors, temperature sensors, and/or pressure sensors, instead of or in addition to the sensor in the measurement port 24. Some sensors may be associated with fastening areas that do not surround a port or an opening of the container 2. They may then be simply placed on the wall of the container 2 (inside or outside), via an attachment or a sensor hatch 25.

The container 2 may have additional elements depending on the application type.

Figure 2:
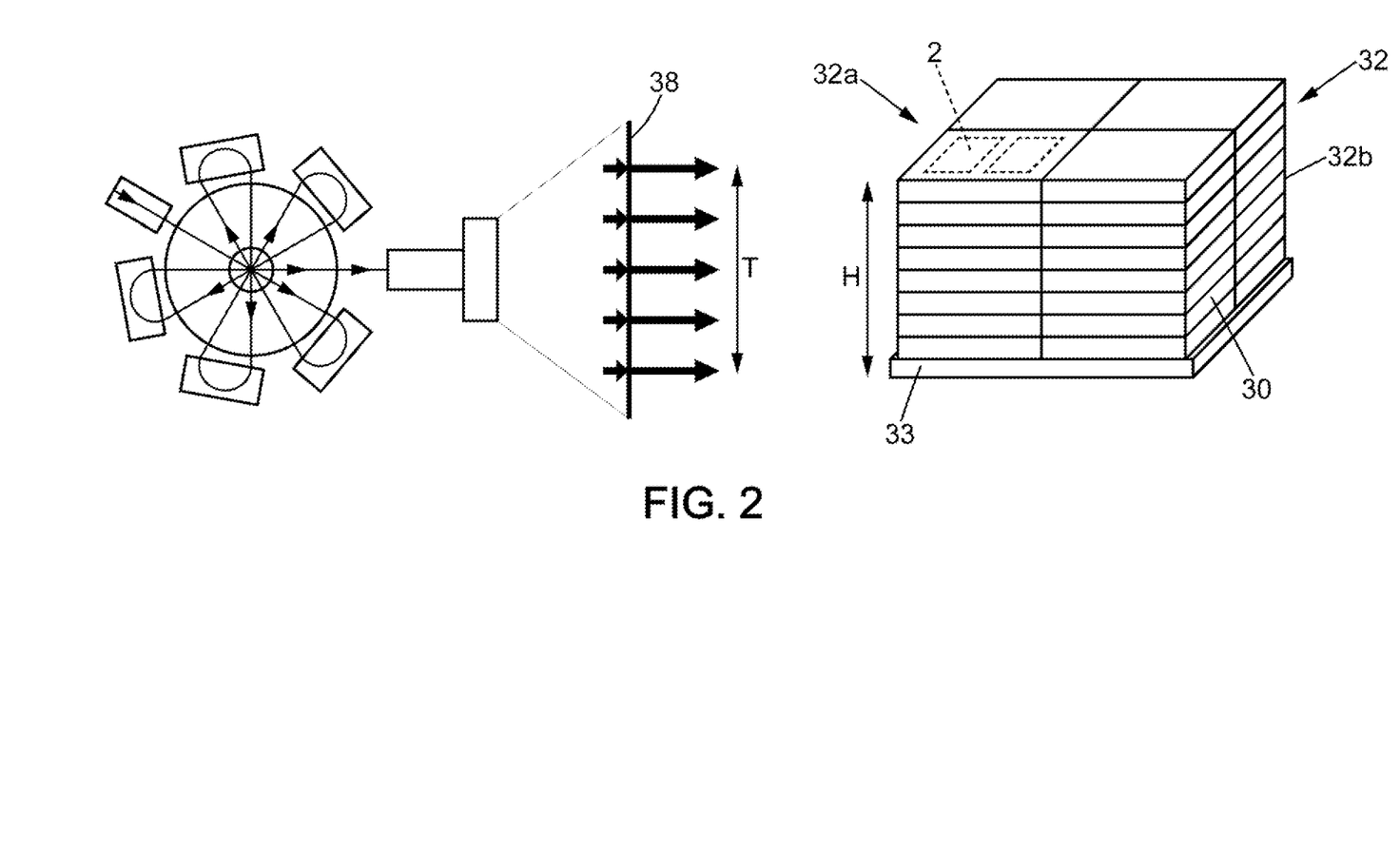
FIG. 2 is a schematic view of an assembly containing several packages, each package containing one or more single-use device(s), the assembly being arranged in front of an X-ray radiation window, according to one embodiment.

The single-use device 2 may be packaged so as to be transported easily and safely from the manufacturing plant to its final destination, and in particular during sterilization thereof. For this purpose, and with reference to FIG. 2, the single-use device 2 may be placed (optionally with other ones) in a package 30 on a support 33 thereby forming an assembly 32 containing one or more stacked package(s). In the example of FIG. 2, for illustration, the package 30 contains four single-use devices 2. The package 30 may contain less than four or more than four single-use devices 2. For example, the package 30 may contain only one single-use device 2. This would for example be the case for a large-size container 2, for example 500 L or more. The single-use device 2 may also be folded, with the shaft 8 optionally retracted, so as to occupy a smaller footprint in the package 30. The single-use devices 2 inside the same package 30 (in the case where the package 30 contains several single-use devices 2) may all have the same orientation, or else have a different orientation. According to one embodiment, the single-use devices 2 may be arranged head-to-tail, in order to make the package 30 more compact, for example.

If the size of the packages allows so, several packages 30 may be arranged on the support 33 superimposed and/or adjacent to each other. The distribution in a stacked arrangement or in an adjacent arrangement of the packages 30 may be selected according to the type and/or size of the single-use device(s) 2. In the example of FIG. 2, the assembly 32 contains four stacks of packages 30, each stack containing eight packages 30.

The support 33 may also have several shapes and sizes. According to the example of FIG. 2, the support 33 is a planar rectangular base, of the tray or pallet type. According to one embodiment, the support 33 has a dimension of 80 cm by 120 cm. According to another embodiment, the support 33 has a dimension of 100 cm by 120 cm. The support 33 may be made of wood and have lateral notches enabling transport thereof. Thus, a forklift may be used to move the support 33. The support 33 may also be put on a conveyor belt.

The support 33 shown in the figures is pallet-shaped. However, the support 33 could be part of a nacelle (also sometimes called a swing). According to one embodiment, the nacelle comprises two trays arranged vertically with respect to each other, each tray being a support for container packages. Thus, the nacelle can transport twice as many products as one single pallet. The nacelle is typically hung from the top, which enables it to be moved forward (via a conveyor) and rotated on its own, as needed.

Since the single-use devices 2 are intended to receive a biopharmaceutical fluid, it is preferable to ensure that the single-use devices 2 are sterile. Indeed, the presence of undesirable micro-organisms in the internal space 4 could cause a reaction or contamination of the biopharmaceutical fluid C. It is then customary to achieve sterility when the single-use device 2 is already packaged and placed on the support 33. The sterilization may be done by X-rays. For this purpose, the assembly 32 located on a conveyor may be conveyed towards a radiation window in order to receive an irradiation dose which would allow eliminating the micro-organisms.

Figure 3:
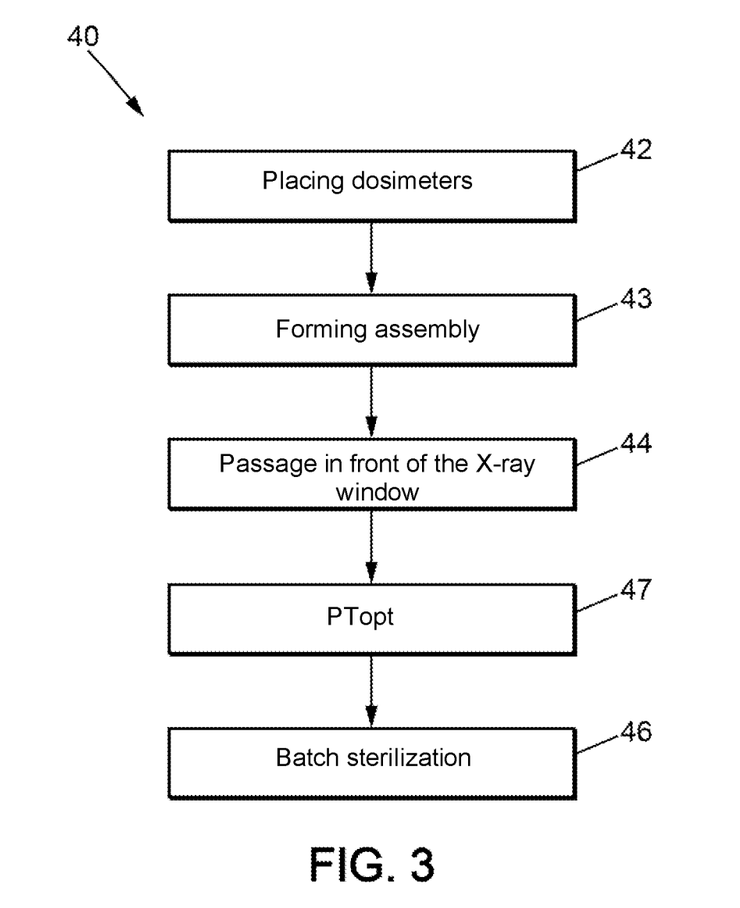
FIG. 3 is a flowchart of a method for sterilizing an assembly comprising at least one single-use device intended to receive a biopharmaceutical fluid, according to one embodiment.

Still with reference to FIG. 2 and complementarily to FIG. 3, a sterilization method 40 uses X-rays in order to sterilize the single-use devices 2 in batches via the sterilization of the assembly 32 comprising the support 33 on which at least one package 30 comprising at least one single-use device, such as the container 2. The single-use device may be a pouch or a filter. For the illustration of the method 40, reference will be made to the case where the single-use device is a container. The container 2 is intended for one single use and intended to receive the biopharmaceutical fluid C. It comprises at least the sensor 27 and the mixing device 7. The assembly 32 may be presented in front of an X-ray radiation window 38 to sterilize a plurality of containers 2 in batches.

The method 40 is particularly suitable in the cases where the density of the container 2 (and consequently of the assembly 32) is heterogeneous. The method 40 allows determining an X-ray irradiation enabling sterilization, and this sterilization is effective in the high-density areas of the container 2 such as the mixing device 7, yet without damaging the sensitive elements of the container 2, such as the sensor 27. A material is said to have a high density when its density is higher than 0.6 g/cm3.

The method 40 is also particularly suitable in the cases where the assembly 32 has a height H which approaches that of the X-ray radiation window 38. Indeed, to proceed with the irradiation, the assembly 32 is presented in front of the radiation window 38. It has been chosen to irradiate a lateral face 32a of the assembly 32 which contains the height H of the assembly 32, the height H being defined as being considered according to a direction normal to the support 33. The height H of the assembly 32 is considered to approach that of the X-ray radiation window 38 when the height H of the assembly is 65% or more of a size T of the X-ray radiation window 38. Indeed, when the size of the product to be irradiated is substantially that of the radiation window 38, the radiation could create edge effects, i.e. areas at the periphery of the radiation window 38 which do not receive the prescribed irradiation. The method disclosed herein allows overcoming, at least in part, these edge effects. According to one embodiment, the assembly has a height 65% or more larger than an X-ray radiation window size. According to one embodiment, the assembly has a height 70% or more larger than an X-ray radiation window size. In one embodiment, the assembly has a height 75% or more larger than an X-ray radiation window size. According to one embodiment, the assembly has a height 80% or more larger than an X-ray radiation window size. According to one embodiment, the assembly has a height 85% or more larger than an X-ray radiation window size. According to one embodiment, the assembly has a height 90% or more larger than an X-ray radiation window size.

The method 40 starts in step 42 with the placement of a plurality (at least two) of dosimeters 50 distributed on and/or in the container 2. Some dosimeters may also be placed on the package 30 and/or the support 33. The dosimeters 50 allow determining a received effective irradiation dose. This data allows ensuring on the one hand that the received dose is above a dose required for the sterilization of the container 2, and on the other hand that the dose does not exceed a value from which a component of the container 2 might be damaged.

The received dose, for a given irradiation, depends on the heterogeneity of the container 2. Indeed, for a given radiation, the density of a material affects the received irradiation dose: the denser the material, the lower the received dose will be. Therefore, at least one dosimeter 50 is arranged on the mixing system 7. The mixing device 7 forms part of the areas of the container with the highest density (compared to the other portions of the container 2). Preferably, several dosimeters are distributed in the areas with the highest density, other than the mixing device 7, in order to control the irradiation dose actually received in different locations of the container 2. According to one embodiment, a high-density area is an area for which the density is locally higher than the average density of the container 2. According to one embodiment, a high-density area is an area for which the density locally is twice greater than the average density of the container 2. High-density areas may be determined based on the considered material and/or material thickness. For example, the following elements may be considered as high-density areas compared to the rest of the container 2, and in particular of the flexible wall 3: the mixing shaft supporting the propellers, the upper and lower bearings including ball bearings.

The density of the package 30 and of the support 33 may be assimilated to the density of the container 2 when determining the high-density areas. Indeed, according to one embodiment, the package 30 is made of cardboard, and the support 33 of wood or steel, the two having a substantially homogeneous construction. Therefore, they do not represent a significant additional density compared to the unpackaged container 2. Consequently, a determination of high-density areas (for the deposition of the dosimeters 50 for step 42) at the level of the container 2 will be considered as a determination of high-density areas at the level of the assembly 32 in general.

On the other hand, a dosimeter 50 is arranged on the sensor 27, in order to ensure that the sensor 27 does not receive an irradiation dose that might damage it. The dosimeter 50 may be arranged on the sensor 27 or in close proximity to the sensor 27, such as for example on the port of the sensor 25. More than one dosimeter 50 may be arranged at the level of the sensor 27.

According to one embodiment, dosimeters 50 are distributed in the fragile areas of the container 2 other than the sensor 27, determined as being likely to be altered if exposed to an excessive dose of X-rays. Indeed, the sensor 27 could be not the only type of element of the container 2 that might be altered by an excessive irradiation dose. The materials forming the wall 3 of the container 2 undergo chemical modifications, feature oxidation of the polymers and the generation of oxidized species inside and over the surface of the polymers, following an excessive exposure to X-rays. This generation of oxidized species may lead to the generation of free radicals and therefore, a modification of the polymers. These free radicals may induce aggregation and oxidation of the product proteins in the single-use biocontainers. Therefore, according to one embodiment, dosimeters 50 are also arranged on the wall 3.

According to one embodiment, several dosimeters 50 are arranged on the sensor(s) 27, and several dosimeters are arranged on the mixing device(s) 7. According to one embodiment, the dosimeters 50 are distributed uniformly on and/or in the container 2. According to another embodiment, the dosimeters 50 are distributed in a non-uniform manner on the container 2, so as to favor the high-density areas and the fragile elements of the container 2.

It is possible to choose as many dosimeters as desired accuracy in the reading of the measurements over the volume of the container 2. The number and the distribution of the dosimeters in and/or on the container 2 affect a mapping of the received irradiation.

There are type I or type II dosimeters. Type I dosimeters can use Fricke's solution, a dichromate solution with spectrophotometric assessment, a ceric-cerous solution with spectrophotometry or potentiometry, or an ethanol-chlorobenzene solution with titration analysis to determine the irradiation dose absorbed during the radiation. Type II dosimeters include process colorimeters, cellulose triacetate, a polymer matrix containing lithium fluoride (photofluorescent), Perspex systems, and radiochromic films and liquids.

In order to place the dosimeters on and/or in the container 2, the container 2 is sacrificed, as it is slashed to enable the installation of the dosimeters 50, and could not be used subsequently according to its common use.

From step 42, we switch to step 43, where the assembly 32 is formed according to a configuration predefined by the arrangement of the container 2 equipped with the plurality of dosimeters 50 in the package 30 then on the support 33. According to one embodiment, if the assembly 32 contains several packages 30 each containing one or more container(s) 2, each container 2 is equipped with dosimeters 50 and is placed in the package 30 and on the assembly 32 in the same manner as it will be during sterilization in batches (step 47) (i.e. according to the predefined configuration), in order to replicate the conditions of passage of the pallets 32 equipped with the package of containers 2 in front of the radiation window 38. Attention is also paid to the orientation of the assembly 32 with respect to the radiation window 38 which is part of the predefined configuration, and to be replicated during step 47 of sterilization in batches.

From step 43, we switch to step 44 which consists in repeating a passage of the assembly 32 containing the container 2 equipped with the plurality of dosimeters 50 in front of the X-ray radiation window 38, according to a first face 32a of the assembly 32 then according to a second face 32b, at different X-ray irradiation power-time pairs. The repetition of passages is done while incrementing the power-time pair between a minimum power-time pair (PTmin) and a maximum power-time pair (PTmax). At each irradiation, the dose received by each dosimeter is recorded for a given power-time pair and for each given face 32a, 32b. According to one embodiment, the assembly 32 successively passes in front of the X-ray radiation window 38 according to the first face 32a then according to the second face 32b at a given power-time pair, before successively passing in front of the X-ray radiation window 38 according to the first face 32a then according to the second face 32b at another given power-time pair, and so on. The first face 32a and the second face 32b are opposite lateral surfaces of the assembly 32. They contain the height H of the assembly 32. Hence, the X-ray radiation window 38 is arranged laterally to the assembly 32 in order to irradiate a lateral surface of the assembly 32. If a top face of the assembly 32 had been preferred for performing the irradiation, the radiation window 38 would have been arranged above the assembly 32.

In order to enable irradiation according to the first lateral face 32a then according to the opposite second lateral face 32b, the assembly 32 is turned over before passing again in front of the X-ray radiation window 38. The turning over corresponds to a 180 degree rotation according to a direction normal to the support 33. The rotation may be done in several ways. The support 33 with the packages 30 and the containers 2 may be lifted and rotated 180 degrees. If the assembly is a nacelle, the nacelle may be turned over by rotation on itself about a vertical pivot by which it is suspended. If the nacelle comprises two supports arranged vertically relative to each other, each support containing packages of containers, so that the pallet-nacelle height is larger than that of the radiation window 38, the position of the nacelle may also be adjusted vertically with respect to the size T of the radiation window 38 in order to irradiate each of the supports of the nacelle.

According to one embodiment, the power-time pairs are pairs taken from among combinations of irradiation power and irradiation time between a minimum power of 75 kW and a maximum power of 1,100 kW, and a minimum irradiation time of 0.1 h and a maximum irradiation time of 20 h. According to one embodiment, the incrementation in irradiation time is done in increments comprised between 0, 1 h and 2 h. According to one embodiment, the incrementation in irradiation power is done in increments comprised between 50 and 200 kW. The incrementation may be constant or variable between each power-time pair.

Since the irradiation doses are cumulative, the same assembly 32 may be irradiated successively and subtracted between each measurement to determine the dose received for a given power-time pair.

Alternatively, it is possible to change the assembly 32 for each measurement, so that the dosimeters 50 receive only one irradiation dose. To this end, a plurality of assemblies 32 containing the dosimeters 50 are prepared in step 42, with the dosimeters 50 positioned identically in each assembly 32, and the containers 2 and packages 30 being in the predefined configuration of the assembly 32. The use of the plurality of assemblies 32 containing the dosimeters 50 for one single passage in front of the radiation window may be preferred because the dosimeters are generally calibrated between 0-~80/100 kGy, limiting a prolonged exposure (>100 kGy).

The incrementation of the power-time pair between a minimum power-time pair (PTmin) and a maximum power-time pair (PTmax) may be done by first varying the powers, then the times, or else by first varying the times, then the powers or by varying both. The minimum and maximum power-time pairs are found experimentally.

The dose received by each dosimeter for irradiation at a power-time pair is recorded so as to create a mapping of the irradiation dose received by each of the plurality of dosimeters according to their position on and/or in the container (and possibly on the package 30 and/or on the support 33) for each of the incremented power-time pairs. If the same assembly 32 containing the dosimeters 50 is subjected more than once to an irradiation power-time pair, one proceeds by subtraction in order to determine the dose actually received for each power-time pair.

The mapping for each irradiation power-time pair may be recorded in a memory for processing in the next step.

From step 44, we switch to step 46, which consists in determining an optimum X-ray radiation power-time pair PTopt. The optimum pair is selected from among the pairs whose mapping has been established in step 44. The optimum power-time pair PTopt is defined as being a power-time pair for which the mapping reveals that after the passage according to the first face 32a and according to the second face 32b all dosimeters 50 record an irradiation dose above a minimum dose Dmin and that the dosimeter associated with the sensor 27 (and generally with the sensitive elements of the container 2) records an irradiation dose below a maximum dose Dmax. The sensitive elements are the elements of the single-use device 2 that deteriorate beyond a predetermined irradiation dose. For example, in the case of the container 2, among the sensitive elements are the sensors, the electronic elements and some mechanical elements. For example, if the sensor 27 involves optical reading through a membrane, the color of the membrane may be deteriorated by too much irradiation, which will distort the reading of the sensor. The same problem may arise for the electrodes of biomass sensors, or dry pH probes. The minimum irradiation dose Dmin is defined as the dose from which sterility is effective. According to one embodiment, the minimum irradiation dose is defined by the standard ISO11137. According to one embodiment, the minimum irradiation dose is at least 25 kGy, preferably at least 27.5 kGy and still more preferably at least 30 kGy. The maximum irradiation dose Dmax is defined as being the dose above which the X-ray irradiation destroys the functionality of a sensor 27 (and more generally of the sensitive elements). According to one embodiment, the maximum irradiation dose Dmax is between 45 and 50 kGy. According to one embodiment, the maximum irradiation dose Dmax is 47 kGy. If the container 2 comprises several sensitive elements, each having an associated level dose from which it deteriorates, a maximum irradiation dose Dmax common to all will preferably be taken as being the lowest of the level doses of the sensitive elements.

Once the optimum power-time pair has been established, we switch to step 47 which consists in sterilizing in batches several assemblies 32 preferably conveyed automatically in front of the radiation window 38 by a conveyor. The irradiation is done at the optimum power-time pair PTopt determined in step 46 on a new assembly 32 comprising a new package 30 and a new container 2 with shapes and sizes identical to those of the previous steps (except for the presence of dosimeters which are absent in step 47). The container 2 and the package 30 are arranged in the predetermined configuration. The irradiation is done according to the first face 32a then the second face 32b of the assembly 32 at the optimum power-time pair PTopt before moving on to another assembly to be irradiated. According to another embodiment, the irradiation takes place at the optimum power-time pair PTopt according to the first face 32a for each assembly 32 to be irradiated, then the assemblies pass again in front of the radiation window 38 but this time according to the second face 32b to be irradiated at the optimum power-time pair PTopt.

The invention claimed is:
1. A method for sterilizing by X-rays an assembly comprising a support and a single-use device for receiving a biopharmaceutical fluid, the density of the assembly being heterogeneous, the assembly having a height of 65% or more of a size of an X-ray radiation window, the height being considered according to a direction normal to the support, the single-use device comprising a sensor and a mixing device, the method comprising:
   placing a plurality of dosimeters distributed on and/or in the single-use device according to a predefined arrangement, one dosimeter being arranged on the sensor and/or on a port of the sensor, and another dosimeter being arranged on the mixing device,
   forming the assembly according to a predefined configuration by arranging the single-use device equipped with the plurality of dosimeters in a package on the support,
   repeating a passage of a first face of the assembly then a second face of the assembly in front of the X-ray radiation window, at several irradiation power-time pairs (PTi), by incrementing irradiation power-time pair between a minimum power-time pair (PTmin) and a maximum power-time pair (PTmax), followed by a mapping of an irradiation dose received by each of the plurality of dosimeters for each of the incremented irradiation power-time pairs; and determining an optimum X-ray radiation power-time pair (PTopt) for which the mapping reveals after passage of the first face and then the second face in front of the X-ray radiation window, all of the plurality of dosimeters record an irradiation dose above a minimum irradiation dose (Dmin) and that the dosimeter associated with the sensor records an irradiation dose below a maximum irradiation dose (Dmax), the minimum irradiation dose (Dmin) being defined as the dose from which sterility is effective, and the maximum irradiation dose (Dmax) being defined as being the irradiation dose at which the X-ray irradiation deteriorates the sensor.

2. The method according to claim 1, further comprising a prior step of determining the maximum dose (Dmax) and/or determining the minimum dose (Dmin).

3. The method according to a claim 2, wherein the single-use device contains a plurality of sensitive elements, the plurality of sensitive elements being defined as elements which deteriorate beyond a predetermined irradiation dose, the sensor forming part of the plurality of sensitive elements, and wherein the step of placing the plurality of dosimeters comprises placing a dosimeter on each of the plurality of sensitive elements, and in the step of determining the optimum X-ray radiation power-time pair (PTopt), the optimum X-ray radiation power-time pair is the pair for which the mapping reveals that all dosimeters record an irradiation dose above the minimum irradiation dose (Dmin) and that the plurality of dosimeters associated with the plurality of sensitive elements record an irradiation dose below the maximum irradiation dose (Dmax), and the maximum irradiation dose (Dmax) being defined as being the lowest irradiation dose from which X-ray irradiation destroys the functionality of one of the plurality of sensitive elements.

4. The method according to claim 3, wherein before each passage of the assembly in front of the X-ray radiation window at a given irradiation power-time pair (PTi), a new plurality of dosimeters which have not yet been irradiated is placed on a new single-use device which has not yet been irradiated according to the predefined arrangement to form a new assembly which has not yet been irradiated.

5. The method according to claim 4, wherein before each passage of the assembly with the second face in front of the X-ray radiation window at an irradiation power-time pair (PTi), a new plurality of dosimeters which have not yet been irradiated is placed on a new single-use device according to the predefined arrangement to form a new assembly which has not yet been irradiated.

6. The method according to claim 5, further comprising the repetition of a passage of the new assembly in front of the X-ray radiation window according to two other opposite faces of the new assembly.

7. The method according to claim 6, further comprising irradiating at the optimum X-ray radiation power-time pair (PTopt) a new assembly comprising a new package and a new single-use device with shapes and sizes identical to those of the previous steps, the new single-use device and the new package being arranged in a predetermined configuration, the irradiation taking place through passage of a first face of the new assembly then a second face of the new assembly in front of the X-ray radiation window.

8. The method according to a claim 1, wherein the single-use device contains a plurality of sensitive elements, the plurality of sensitive elements being defined as elements which deteriorate beyond a predetermined irradiation dose, the sensor forming part of the plurality of sensitive elements, and wherein the step of placing the plurality of dosimeters comprises placing a dosimeter on each of the plurality of sensitive elements, and in the step of determining the optimum X-ray radiation power-time pair (PTopt), the optimum X-ray radiation power-time pair is the pair for which the mapping reveals that all dosimeters record an irradiation dose above the minimum irradiation dose (Dmin) and that the plurality of dosimeters associated with the plurality of sensitive elements record an irradiation dose below the maximum irradiation dose (Dmax), and the maximum irradiation dose (Dmax) being defined as being the lowest irradiation dose at which X-ray irradiation destroys the functionality of one of the plurality of sensitive elements.

9. The method according to claim 1, wherein before each passage of the assembly in front of the X-ray radiation window at a given irradiation power-time pair (PTi), a new plurality of dosimeters which have not yet been irradiated is placed on a new single-use device according to the predefined arrangement to form a new assembly which has not yet been irradiated.

10. The method according to claim 1, wherein before each passage of the second face of the assembly in front of the X-ray radiation window at an irradiation power-time pair (PTi), a new plurality of dosimeters which have not yet been irradiated is placed on a new single-use device with the predefined arrangement to form a new assembly which has not yet been irradiated.

11. The method according to claim 1, wherein the minimum irradiation dose (Dmin) is defined by the standard ISO11137.

12. The method according to claim 1, wherein the minimum irradiation dose (Dmin) is at least 25 kGy, or at least 27.5 kGy, or at least 30 kGy.

13. The method according to claim 12, wherein the maximum irradiation dose (Dmax) is between 45 and 50 kGy, or 47 kGy.

14. The method according to claim 1, wherein the irradiation power-time pairs (PTi) are pairs taken from among combinations of irradiation power and irradiation time comprised between a minimum power of 75 kW and a maximum power of 1,100 kW, and a minimum irradiation time of 0.1 hours and a maximum irradiation time of 20 hours.

15. The method according to claim 1, wherein a time increment of the irradiation is done in increments comprised between 0.1 hours and 2 hours.

16. The method according to claim 1, wherein a power increment of the irradiation is done in increments comprised between 50 and 200 kW.

17. The method according to claim 1, further comprising the repetition of a passage of the assembly in front of the X-ray radiation window according to two other opposite faces of the assembly.

18. The method according to claim 1, wherein the package comprises several single-use devices and/or the assembly comprises several packages arranged on the support.

19. The method according to claim 1, further comprising irradiating at the optimum X-ray radiation power-time pair (PTopt) a new assembly comprising a new package and a new single-use device with shapes and sizes identical to those of the previous steps, the new single-use device and the new package being arranged in the predefined configuration, the irradiation taking place to a first face then a second face of the new assembly.

* * * * *